United States Patent
Carroll (10) Patent No.: US 8,245,707 B2
(45) Date of Patent: Aug. 21, 2012

(54) ANTI-FOG BREATHING APPARATUS FOR THE ELIMINATION OF BREATH VAPOR CONDENSATION ON THE SURFACES OF PROTECTIVE EYE LENSES ASSOCIATED WITH RECREATIONAL EQUIPMENT

(76) Inventor: Fleming Vaughn Carroll, Clemmons, NC (US)

( * ) Notice: Subject to any disclaimer, the term of this patent is extended or adjusted under 35 U.S.C. 154(b) by 1069 days.

(21) Appl. No.: 12/217,690

(22) Filed: Jul. 8, 2008

(65) Prior Publication Data

US 2009/0038058 A1    Feb. 12, 2009

Related U.S. Application Data

(60) Provisional application No. 60/958,841, filed on Jul. 9, 2007.

(51) Int. Cl.
  *A62B 18/08* (2006.01)
(52) U.S. Cl. .......... 128/201.26; 128/201.25; 128/206.29
(58) Field of Classification Search ............ 128/200.29, 128/201.11, 201.15, 201.22, 201.23, 201.26, 128/201.27, 206.21, 206.22, 206.28, 206.29, 128/205.29; 2/6.2, 8.2, 422, 424
See application file for complete search history.

(56) References Cited

U.S. PATENT DOCUMENTS

| | | | | |
|---|---|---|---|---|
| 1,210,939 A * | 1/1917 | Hilgers | ..................... | 128/201.11 |
| 4,207,882 A * | 6/1980 | Lemere | ..................... | 128/206.15 |
| 4,230,106 A * | 10/1980 | Geeslin et al. | ........... | 128/201.11 |
| 4,334,533 A * | 6/1982 | Henkin | ..................... | 128/205.28 |
| 4,634,117 A * | 1/1987 | Kramer | ..................... | 482/13 |
| 4,719,911 A * | 1/1988 | Carrico | ..................... | 128/206.29 |
| 4,878,491 A * | 11/1989 | McGilvray, III | ......... | 128/201.11 |
| 4,896,664 A * | 1/1990 | Harayama | ................ | 128/200.25 |
| 5,485,832 A * | 1/1996 | Joffity | ..................... | 128/201.11 |
| 5,697,362 A * | 12/1997 | Albrecht | .................. | 128/201.11 |
| 6,684,882 B1 * | 2/2004 | Morine | ..................... | 128/206.11 |
| 6,920,880 B1 | 7/2005 | Zahrt et al. | | |
| 6,971,386 B2 * | 12/2005 | Duxbury | .................. | 128/205.27 |
| 2002/0104533 A1 * | 8/2002 | Kalhok et al. | ........... | 128/201.24 |
| 2004/0003810 A1 * | 1/2004 | Templeton et al. | ...... | 128/201.22 |
| 2004/0221841 A1 * | 11/2004 | Herschel | .................. | 128/201.26 |
| 2007/0131227 A1 * | 6/2007 | Wheelwright | ........... | 128/201.22 |

* cited by examiner

*Primary Examiner* — Loan Thanh
*Assistant Examiner* — Kathryn D Sheikh
(74) *Attorney, Agent, or Firm* — Kilpatrick Townsend & Stockton LLP (57) ABSTRACT

A breathing apparatus used in conjunction with eye glasses, goggles, face masks or helmets each containing eye protection elements to restrict/eliminate the presence of breath vapor condensing on the surface of said equipment containing eye lenses while being worn primarily during sport and recreational activity. The breathing apparatus, through the containment of breath vapor at its source, moves vapor away from said eye lenses by use of a snorkel assembly containing: mouthpiece, multi-port manifold, flexible tubing terminating in dual function breath exhaust/entry sub-assembly. Device may be positioned above wearer's shoulders and secured to his/her neck by means of a tension and position-adjusting strap. Not only is this apparatus presented as an ACCESSORY to be worn along with said eye protection sports equipment but will also be INTEGRATED INTO THE DESIGN AND MANUFACTURE of a face mask for use in sport and recreation activities such as paintball.

7 Claims, 7 Drawing Sheets

ANTI-FOG BREATHING APPARATUS FOR THE ELIMINATION OF BREATH VAPOR CONDENSATION ON THE SURFACES OF PROTECTIVE EYE LENSES ASSOCIATED WITH RECREATIONAL EQUIPMENT

CROSS-REFERENCE TO RELATED APPLICATIONS

Upon the filing of this application, applicant (Fleming V. Carroll) wishes to claim benefit of provisional patent filing No. 60/958,841; dated: Jul. 9, 2007; titled: Anti-Fog Breathing Apparatus for Use With Paintball Mask.

BACKGROUND OF THE INVENTION

This invention relates generally to the field of recreational equipment worn to protect one's eyes while in pursuit of a variety of activities wearing goggles, a facemask or a helmet, all of which are susceptible to fogging due to breath vapor condensation frequently resulting in poor or no visibility. The invention is generally directed to a breathing apparatus used to restrict/eliminate the condensing of wearers' breath vapor on protective lenses, such as goggles or a facemask.

Manufacturers of sporting goods equipment containing protective eye lenses have made strides in improving lens performance often altering breathable materials used to either encase or surround a lens as found in a pair of goggles while others choose to alter the design of perforations molded into the materials surrounding the lens as found in a paintball mask, each trying to affect air ventilation around the lens. Battery powered ventilation fan units, dual pane or thermal lenses provide thermal insulation between inner and outer lenses of complete lens assembly and protective coatings applied to lenses at the time of manufacturing are among the current industry standards in attempting to control breath vapor condensing onto lens surfaces. Most sportsmen continue to prep their lenses before play using any one of many spray coating/cleaners used to reduce fogging only to reapply spray coating or simply wipe moisture off lenses with a dry cloth before continuing play.

The manufacturers of this equipment and technologies and those individuals who use this equipment and/or product have all experienced limited success when attempting to control or eliminate the problem of fogging of eye lenses on their equipment.

Attempting to resolve the problem of fogged eye lenses, U.S. Pat. No. 6,920,880applicants claimed that the mask defogging system and method SHOULD enable the wearer to defog the interior of a face mask of breath vapor, thus removing the breath vapor accumulated on the lens of the mask. Furthermore, one who is skilled in the art of defogging a mask may realize that this system may reintroduce a sizeable percentage by volume, of breath vapor moving through the mouthpiece airway as presented by both the description and illustrations contained in said document. Furthermore, vapor which does travel to its exhaust port might well be redeposited at least in part onto the outside/exterior of the facemask as indicated by way of illustrations, thus setting up the situation of the lenses now having breath vapor condensation on both the interior and exterior of the lens of this mask.

SUMMARY OF INVENTION

The primary objective of this invention is to provide a means by which people involved in both sport and recreational activity may pursue their passion perhaps or endeavors, free of the restriction created by the condensing of their own breath vapor onto any variety of eye lens, protection devices they may be wearing.

The breathing apparatus of this invention comprises a snorkel like device consisting of a comfortable, angled mouthpiece; directional multi-port manifold, flexible tubing, dual function breath exhaust/entry sub-assembly; debris shields and filters as well as adjustable retaining strap.

Having read the detailed description of this invention and viewed supportive drawings one will recognize that this invention will afford not only uninterrupted fog free breathing while actively pursuing recreational activities, but will advance existing technology in this field by improving designs relating to ventilation, comfort, visibility, protection, flexibility and styling.

DETAILED DESCRIPTION OF INVENTION

Figure 1:
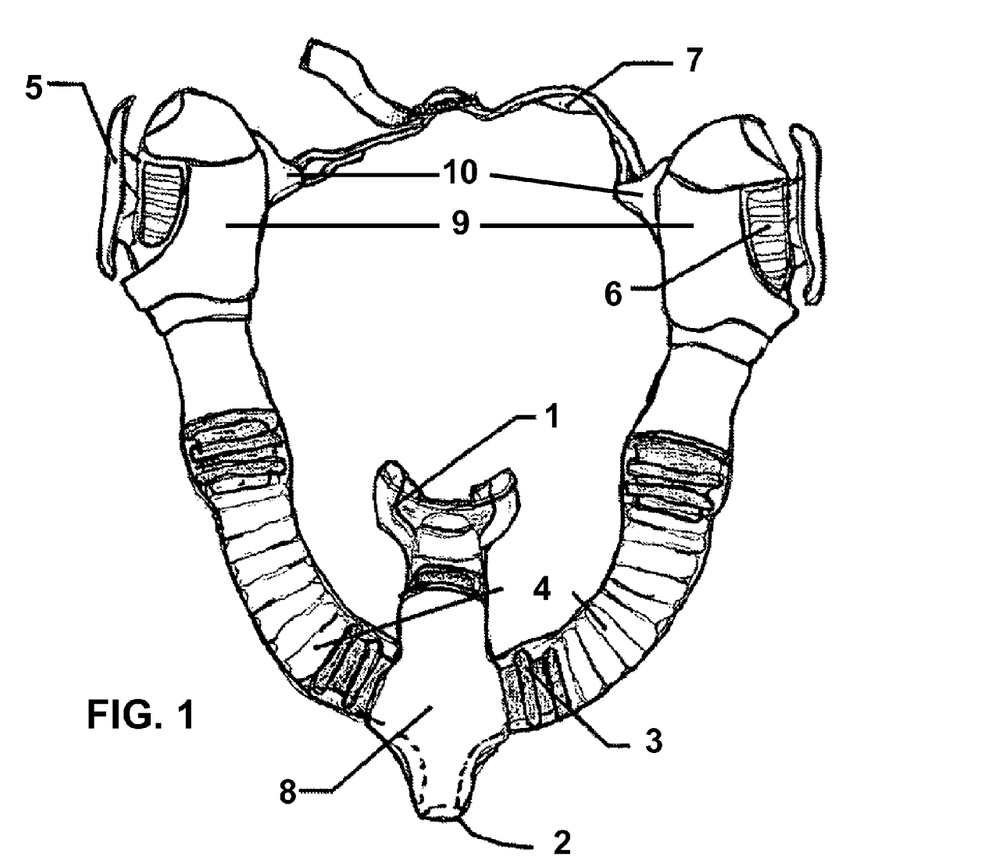
FIG. 1 is an anti-fog breathing apparatus according to one embodiment of the invention.
Figure 2A:
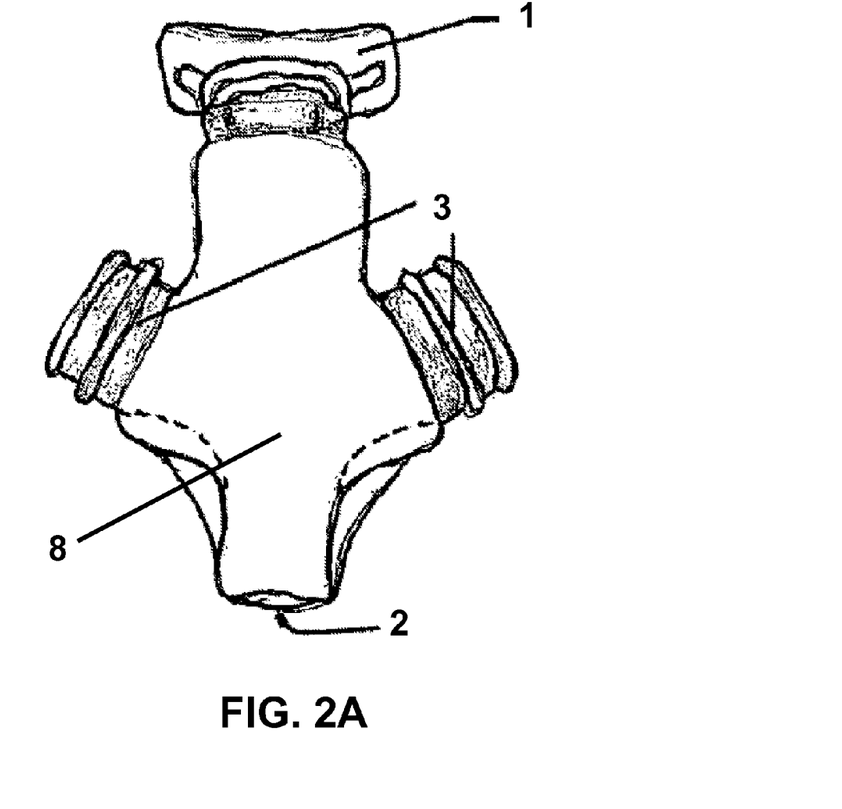
FIG. 2A is an illustration of components of an anti-fog breathing apparatus according to one embodiment of the invention.
Figure 2B:
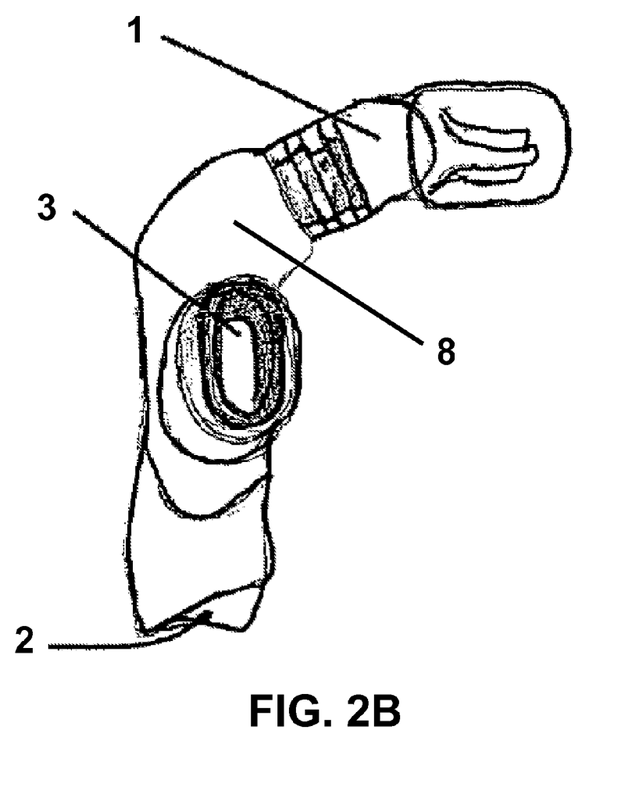
FIG. 2B is an illustration of components of an anti-fog breathing apparatus according to one embodiment of the invention.
Figures 3A, 3B, 3C:
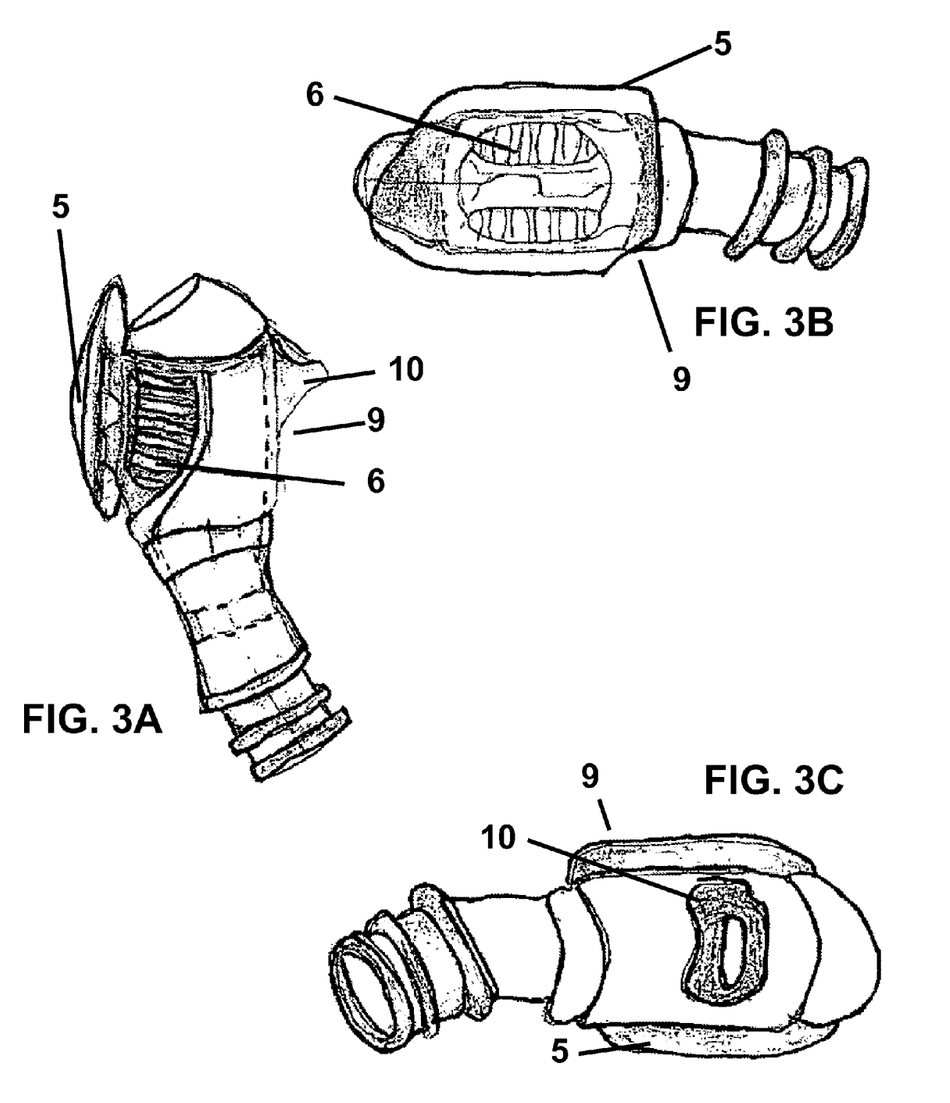
FIG. 3A is an illustration of components of an anti-fog breathing apparatus according to one embodiment of the invention
FIG. 3B is an illustration of components of an anti-fog breathing apparatus according to one embodiment of the invention.
FIG. 3C is an illustration of components of an anti-fog breathing apparatus according to one embodiment of the invention.
Figure 4A:
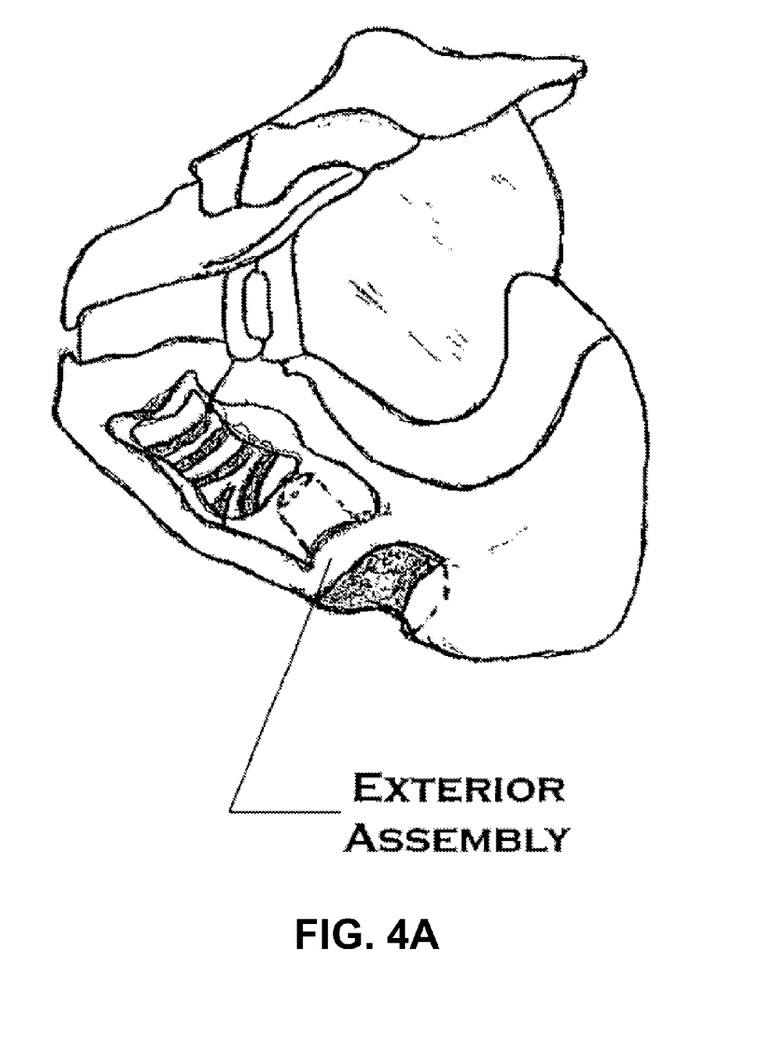
FIG. 4A is an anti-fog facemask according to one embodiment of the invention.
Figure 4B:
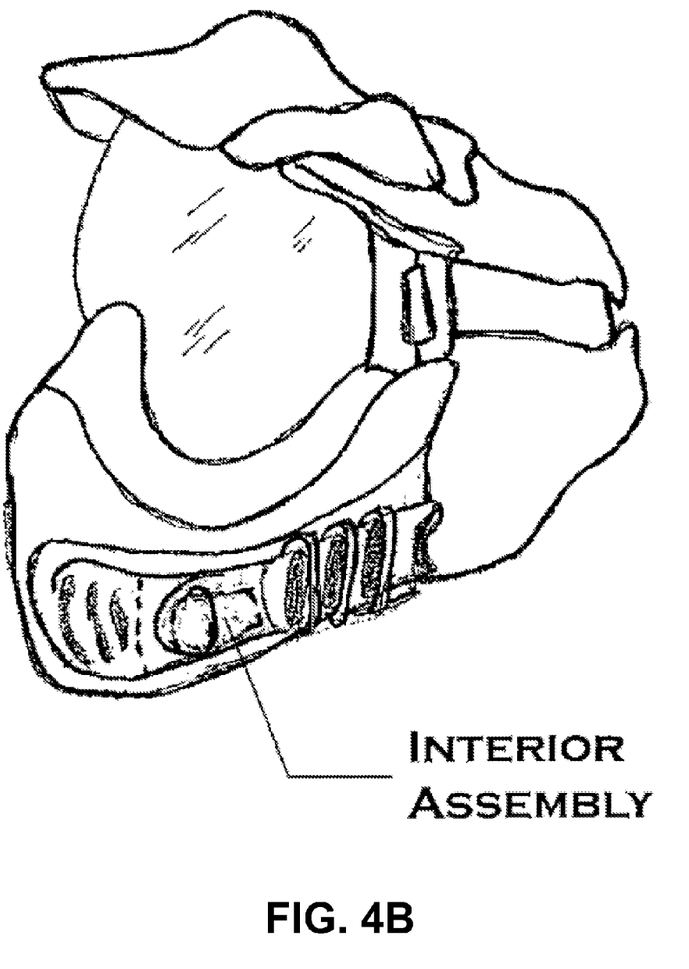
FIG. 4B is an anti-fog facemask according to one embodiment of the invention.
Figure 4C:
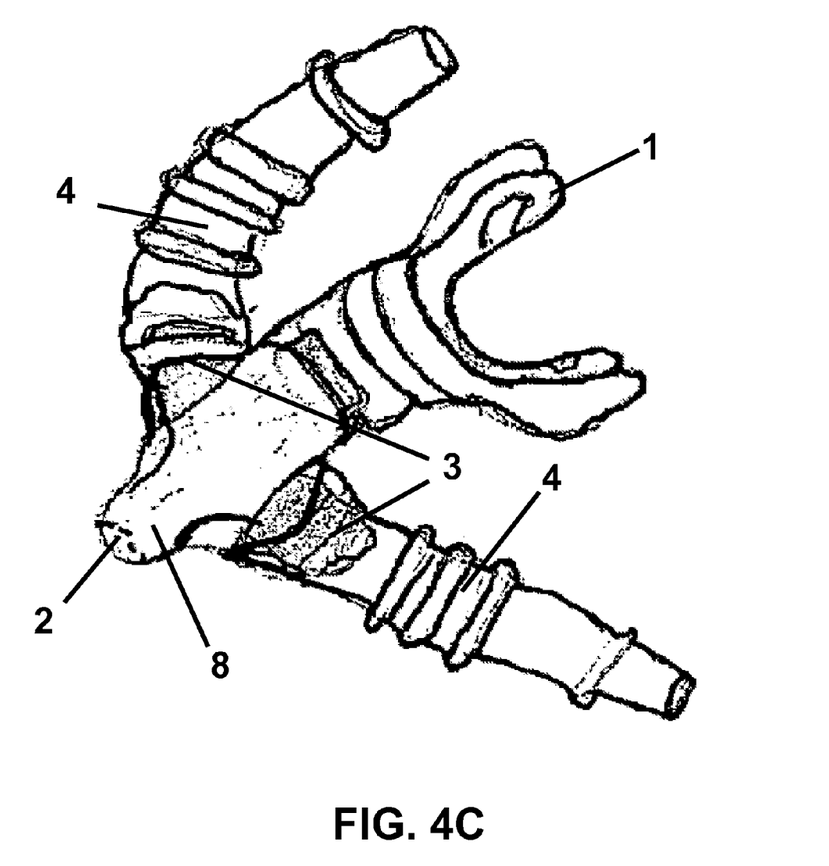
FIG. 4C is an illustration of a component of an anti-fog facemask according to one embodiment of the invention.

A breathing apparatus used in conjunction with equipment containing eye protective lenses such as eye glasses, eye goggles, face masks, and helmets containing visors or shields to restrict/eliminate the presence of breath vapor condensing on the eye lenses of such equipment while in pursuit of sport and recreational activities. Since breath vapor is not present within the space between the face mask and the wearers' face and is removed from the area surrounding eye glasses and goggles, while using this invention, vapor cannot condense on the inside of the tens and thus restrict the visibility of the wearer due to the presence of said breath vapor. This is achieved through the assembly of traditional swimming snorkel design elements into a breathing apparatus used to control the presence of breath vapor while allowing wearer freedom from restricted air volume when breathing through said invention. Free breathing by wearer and his/her subsequent control of the presence of breath vapor within the mask or goggles is achieved by the inhaling and exhaling of air through one's mouth. Referring now to FIG. 1 the mouthpiece 1 of invention is held in place by wearer's teeth and lips. Both air intake and exhausting of breath are directed through the manifold 8 containing three ports or openings, namely a bottom port 2 and left and right side ports 3 each functioning as points of both air exhaust and intake. These multi-ports ease the inherent restriction to the wearer of breathing through such an apparatus often found in prior art. The articulation of these ports 2 & 3 produce large volumes of air available to invention wearer thus minimizing breathing noises which might otherwise be emitted by other breathing apparatus design when worn for sports or recreational activity. As breath is directed through mouthpiece 1 and into the manifold 8 the majority of breath and its inherent vapor is exhausted through the port 2 located directly below mouthpiece by the way of proximity and restricting, funneling design of lower end on manifold 2 where it is exhausted away from the interior of the mask or helmet face shield and away from eye glasses or goggles. Lesser quantities of breath vapor will travel out of manifold 8 and into one of the two dual angled side ports 3 therein. Manifold side ports have a length of flexible tubing 4 attached there to which the exhaust breath makes its way through as it approaches dual function breath exhaust/entry sub-assemblies 9. It should be apparent to the viewer by way of renderings who breath exhaust will pass into the apparatus and be dispersed away from the wearer's body. The inhaling of air by player is simply the reverse path of the exhaled breath and vapor. Shape of the manifold 8 allows the greater amounts of inhaled air to originate from each of the dual function breath exhaust/entry sub-assemblies 9 located behind the wearers head. Lesser-inhaled air is derived from the primary exhaust port 2 of the manifold 8 helping deliver fresh air to player. Not only does this invention deliver its claims of rendering fog-free visibility through the lenses of protective equipment worn by player and allowing said player generous supply and exhausting of breath due to this inventions design, moreover unobstructed breathing by wearer is further insured by screening grids 6 covering the air exhaust/entry orifices in the dual function breath exhaust/entry sub-assemblies 9. Protective shields 5 protect screening grids 6 and the air exhaust/entry orifices from paint bursts, bug splat and general debris resulting in unobstructed breathing. Furthermore, the presence of flexible tubing 4 positioned above player's shoulders may be appreciated should player receive a neck shot by an opponent while pursuing activities such as paintball.

Invention has been previously described as an accessory breathing apparatus wherein its wearer places the mouthpiece 1 of invention into their mouth. The other end of the apparatus is positioned above wearer's shoulders and secured to wearer's neck just below mask or goggles by means of a tension and position adjusting straps 7. Should wearer wish to talk perhaps to a team member, they merely have to release their mouths grasp on the comfortably angled mouthpiece 1 whereby mouthpiece and manifold fall from in front of mouth to allow speech. Granted, wearer must re-insert manifold mouthpiece 1 by hand for continued, comfortable, protected, quiet, free breathing, fog free visibility through equipment lenses in any and all seasons of the calendar year and resultant in all ambient air temperature and humidity levels. The present invention is presented as first an accessory to be worn in conjunction with a player's facemask, goggles, or helmet and thereby delivering the various claims described herein. This invention is not represented as an item to be attached, to retrofit onto or converted into another piece of equipment by user. Such action by user might disqualify them from an organized event as the modification of equipment is often disallowed. Furthermore liability issues may arise from injury received by a player who has attached to, modified or altered a manufacturer's equipment.

Manufacturers of goggles and face masks have made strides in improving designs relating to ventilation, comfort, protection, flexibility and styling yet, it is known by these manufacturers and by those individuals who use this equipment that these goggles and face masks do not keep a considerable percentage of a player's lenses from fogging. It would be appropriate to state that not all sports enthusiasts or recreational participants have the problem of their lenses fogging during play. While the invention has been described to in conjunction with a specific mode, it is apparent that alternatives, modifications and variations may be realized here upon. It is perceived pursuant to the filing of this application for non-provisional patent, intellectual property rights will be upheld for this inventor's benefit embodying both this title of invention ANTI-FOG BREATHING APPARATUS FOR THE ELIMINATION OF BREATH VAPOR CONDENSATION ON THE SURFACES OF PROTECTIVE EYE LENSES ASSOCIATED WITH SPORTS AND RECREATIONAL EQUIPMENT and the evolution of its variations.

What is claimed is:

1. An anti-fog breathing apparatus comprising:
   a dual tube snorkel device comprising:
      an angled mouthpiece defining an airway;
      a directional triple port manifold connected to the mouthpiece, wherein the directional triple port manifold comprises a central bottom port, a right side port and a left side port, and wherein the central bottom port, the right side port and the left side port are both air intake and exhaust ports;
      a first flexible tube connected to the right side port and a second flexible tube connected to the left side port;
      a first dual function breath exhaust/entry sub-assembly connected to the first flexible tube and a second dual function breath exhaust/entry sub-assembly connected to the second flexible tube, wherein the dual function breath exhaust/entry sub-assemblies each define an opening covered by a debris screening grid, wherein the debris screening grid is shielded by a protective shield; and
   a tension and position adjustable strap having a first end attached to the first sub-assembly and a second end attached to the second sub-assembly.

2. The anti-fog breathing apparatus of claim 1 wherein the directional triple port manifold is funnel-shaped adjacent to the central bottom port.

3. An anti-fog breathing apparatus comprising:
   a facemask;
   a dual tube snorkel device coupled to the facemask comprising:
      an angled mouthpiece defining an airway;
      a directional triple port manifold connected to the mouthpiece, wherein the directional triple port manifold comprises a central bottom port, a right side port and a left side port, and wherein the central bottom port, the right side port and the left side port are both air intake and exhaust ports;
      a first flexible tube connected to the right side port and a second flexible tube connected to the left side port;
      a first dual function breath exhaust/entry sub-assembly connected to the first flexible tube and a second dual function breath exhaust/entry sub-assembly connected to the second flexible tube, wherein the dual function breath exhaust/entry sub-assemblies each define an opening covered by a debris screening grid, wherein the debris screening grid is shielded by a protective shield; and
   a tension and position adjustable strap having a first end attached to a first side of the facemask and a second end attached to a second side of the facemask.

4. The anti-fog breathing apparatus of claim 3, wherein the directional triple port manifold is funnel-shaped adjacent to the central bottom port.

5. The anti-fog breathing apparatus of claim 3, wherein the first dual function breath exhaust/entry sub-assembly is molded into the first side of the facemask and the second dual function breath exhaust/entry sub-assembly is molded into the second side of the facemask.

6. The anti-fog breathing apparatus of claim 3, wherein the first flexible tube is attached to the first dual function breath exhaust/entry sub-assembly and the second flexible tube is attached to the second dual function breath exhaust/entry sub-assembly at positions external to the facemask.

7. The anti-fog breathing apparatus of claim 3, wherein the first flexible tube is attached to the first dual function breath exhaust/entry sub-assembly and the second flexible tube is attached to the second dual function breath exhaust/entry sub-assembly at positions internal to the facemask.

\* \* \* \* \*